United States Patent
Dewing et al.

(10) Patent No.: US 7,244,231 B2
(45) Date of Patent: Jul. 17, 2007

(54) SYSTEM AND METHOD FOR ASSESSING THE FUNCTIONAL ABILITY OR MEDICAL CONDITION OF AN ACTOR

(75) Inventors: Wende L. Dewing, Minneapolis, MN (US); Larry L. Stickler, Eden Prairie, MN (US); Christopher A. Miller, St. Paul, MN (US); Karen Z. Haigh, Greenfield, MN (US); Rose Mae M. Richardson, Roseville, MN (US); Rand P. Whillock, North Oaks, MN (US); Stephen D. Whitlow, Rogers, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/703,097

(22) Filed: Nov. 6, 2003

(65) Prior Publication Data

US 2004/0147817 A1    Jul. 29, 2004

Related U.S. Application Data

(60) Provisional application No. 60/424,257, filed on Nov. 6, 2002.

(51) Int. Cl.
*A61B 5/00*    (2006.01)

(52) U.S. Cl. ............... 600/300; 600/301; 128/920; 705/2

(58) Field of Classification Search ........ 600/300–301; 128/903–905, 920–921; 434/235–238, 262; 340/539, 573–576; 705/2–4; 482/4, 8–9
See application file for complete search history.

(56) References Cited

U.S. PATENT DOCUMENTS 4,259,548 A    3/1981    Fahey et al.

(Continued)

FOREIGN PATENT DOCUMENTS

EP    0 558 975 A1    2/1993

(Continued)

OTHER PUBLICATIONS

PCT Search Report mailed Oct. 24, 2005 (6 pgs).

*Primary Examiner*—Max F. Hindenburg
*Assistant Examiner*—Michael C Astorino
(74) *Attorney, Agent, or Firm*—Kris T. Fredrick

(57) ABSTRACT

A system and method for assessing a functional or medical ability of an actor in a environment. The method includes providing a plurality of data sources in the environment. One or more of the data sources are designated as providing information relating to a functional or medical ability. Data from the designated data sources is retrieved and forms the basis of a functional or medical ability evaluation. In one embodiment, a plurality of baseline function categories are established, with information from one or more of the data sources being assigned to at least one of the baseline function categories.

50 Claims, 6 Drawing Sheets

U.S. PATENT DOCUMENTS

| | | |
|---|---|---|
| 4,665,385 A | 5/1987 | Henderson |
| 4,803,625 A | 2/1989 | Fu et al. |
| 4,952,928 A | 8/1990 | Carroll et al. |
| 5,036,462 A | 7/1991 | Kaufman et al. |
| 5,045,839 A | 9/1991 | Ellis et al. |
| 5,086,385 A | 2/1992 | Launey et al. |
| 5,228,449 A | 7/1993 | Christ et al. |
| 5,311,185 A | 5/1994 | Hochstein et al. |
| 5,400,246 A | 3/1995 | Wilson et al. |
| 5,410,471 A | 4/1995 | Alyfuku et al. |
| 5,441,047 A | 8/1995 | David et al. |
| 5,997,476 A * | 12/1999 | Brown ............ 600/300 |
| 6,238,337 B1 * | 5/2001 | Kambhatla et al. ...... 600/300 |
| 6,280,198 B1 * | 8/2001 | Calhoun et al. ......... 434/236 |
| 6,280,380 B1 | 8/2001 | Bardy |
| 6,524,239 B1 * | 2/2003 | Reed et al. ............ 600/300 |
| 2002/0019586 A1 | 2/2002 | Teller et al. |
| 2003/0083822 A2 * | 5/2003 | Brunner et al. ............ 705/2 |

FOREIGN PATENT DOCUMENTS

WO     WO 01/075653 A3    10/2001

* cited by examiner

SYSTEM AND METHOD FOR ASSESSING THE FUNCTIONAL ABILITY OR MEDICAL CONDITION OF AN ACTOR

CROSS-REFERENCE TO RELATED APPLICATIONS

This application is related to, and is entitled to the benefit of, U.S. Provisional Patent Application Ser. No. 60/424,257, filed Nov. 6, 2002, the teachings of which are incorporated herein by reference.

BACKGROUND OF THE INVENTION

The present invention relates to an automated system and method for assessing the functional ability or medical condition (or medical ability) of an actor. More particularly, it relates to a system and method that utilizes multiple sensors and/or interface device(s) to gather functional ability and/or medical condition data relating to the actor, assess the gathered data, and report the assessment and gathered data to persons interested in the actor's welfare such as a caregiver, including alerting those persons to potential emergency situations. Potential domains include in-home monitoring systems, eldercare, and workplace environments (including hazardous work environments) to name but a few.

Elderly people commonly suffer from diminishing physical and/or mental capabilities. Similarly, younger persons suffering from certain maladies (e.g., stroke, disease, etc.) will invariably lose their ability to function independently. In these and other cases, attending physicians (or other caregiver) need to be apprised of changes in the patient's functional ability or medical condition to provide early detection and possible prevention of acute medical conditions.

Currently, gathering of potentially applicable information relating to a patient's functional ability or medical condition is done only as part of a direct, face-to-face interview between the caregiver and the patient. During these periodically-scheduled sessions (e.g., monthly), the caregiver asks the patient a series of questions and generally observes the patient for a short time (e.g., one hour or less). Unfortunately, while a drastic change in the patient (as compared to a previous session) can be identified, it is difficult at best for the caregiver to obtain a true picture of the patient's mental and/or physical capabilities, and in particular to notice slow or incremental deterioration in either facet over time. For example, a typical line of inquiry will relate to the patient's sleeping patterns. For most patients, the response to such a question will inherently be based upon their recollection of the immediately preceding one or two days. Thus, a patient experiencing gradually worsening sleep patterns, but who happened to have a restful night the evening before the caregiver meeting, may report that everything is fine. Further, it is difficult for patients to accurately recall and/or gauge their functional abilities over extended periods of time (e.g., more than a few days). Also, many patients, especially elderly individuals, become nervous or confused when answering questions at an unfamiliar location remote from the patient's home such as a caregiver's office. Again, this problem greatly impedes the caregiver's ability to properly evaluate the patient's actual mental and physical capabilities.

To overcome the above concerns, efforts have been made to develop in-home devices that record information potentially related to a patient's physical and/or mental capabilities. For example, automated pill dispensers are available that record times at which medication is dispensed. In theory, this information can be viewed as being indicative of the patient's mental capabilities in terms of remembering to take prescribed medication. Of course, actuation of the dispenser does not necessarily mean that the dispensed medication was ingested by the patient. Further, and perhaps more importantly, this information presents only one small piece of an overall assessment of the patient. That is to say, numerous other functional/medical condition information is required to accurately assess the patient's abilities, especially as part of a long-term assessment. More technically advanced devices, such as an in-home pacemaker data transmitter, are similarly limited. Thus, while individual devices are available to record information potentially related to a patient's functional abilities and medical condition, direct caregiver interaction/patient interviews are still required, and result in the deficiencies described above.

Alternatively, the patient-caregiver visits can be scheduled on a more frequent basis or a live-in caregiver can be provided. While this may facilitate accumulation of more data points, either approach is quite costly and relies upon the availability of trained personnel. Unfortunately, in most situations the enormous costs and/or lack of qualified caregivers prohibits implementation of either approach.

Periodic, face-to-face patient interviews, while well accepted, are simply inadequate for caregivers to reliably assess the physical and/or mental capabilities of a patient. This is especially true where a long-term assessment of gradually diminishing abilities is of importance or where precursors to certain health emergencies occur (e.g., symptoms of stroke (or fall) often appear several days before the stroke itself) and the ability to identify these symptoms in advance of the event could allow a caregiver to reduce the potential effect of the event. Similar concerns arise in other domains, such as persons working in a hazardous environment where knowing the worker's functional ability could alert others as to potential problems (e.g., exposure to hazardous gases, fatigue, hypoxia, etc.). Even further, actors or workers in less rigorous environments (e.g., assembly line or warehouse) are also susceptible to diminished functional abilities that, if identified in a timely fashion, can be quickly addressed. Unfortunately, other than face-to-face interviews, persons concerned with actors in these environments do not have access to highly relevant, day-to-day information. Therefore, a need exists for a system and method for automated generation, storing and assessment of multiple data sets from multiple sensors relating to certain functions and/or medical conditions of an actor.

SUMMARY

One aspect of the present invention relates to a method of assessing functional or medical ability of an actor in an environment. The method includes providing a plurality of data sources in the environment. One or more of the data sources are designated as providing information relating to a functional or medical ability. Data from the designated data sources is retrieved and forms the basis of a functional ability evaluation. In one preferred embodiment, a plurality of baseline function categories are established, with information from one or more of the data sources being assigned to at least one of the baseline function categories. In another, related embodiment, the functional or medical ability evaluation is based upon information from two or more of the baseline function categories.

Another aspect of the present invention relates to a system for assessing functional or medical ability of an actor in a daily living environment. The system includes a plurality of data sources and a controller. The controller is adapted to designate one or more of the data sources as providing information relating to a functional or medical ability and retrieve data from the designated data sources. Further, the controller is adapted to automatically evaluate a functional or medical ability of the actor based upon the retrieved information. In one embodiment, the system further includes an actor interface device adapted to selectively interact with the actor. With this embodiment, the controller is further adapted to retrieve responses of the actor to operation of the actor interface device for use in evaluating functional or medical ability. In another, related embodiment, the actor interface device is adapted to engage the actor in a game.

DETAILED DESCRIPTION OF THE PREFERRED EMBODIMENTS

Figure 1:
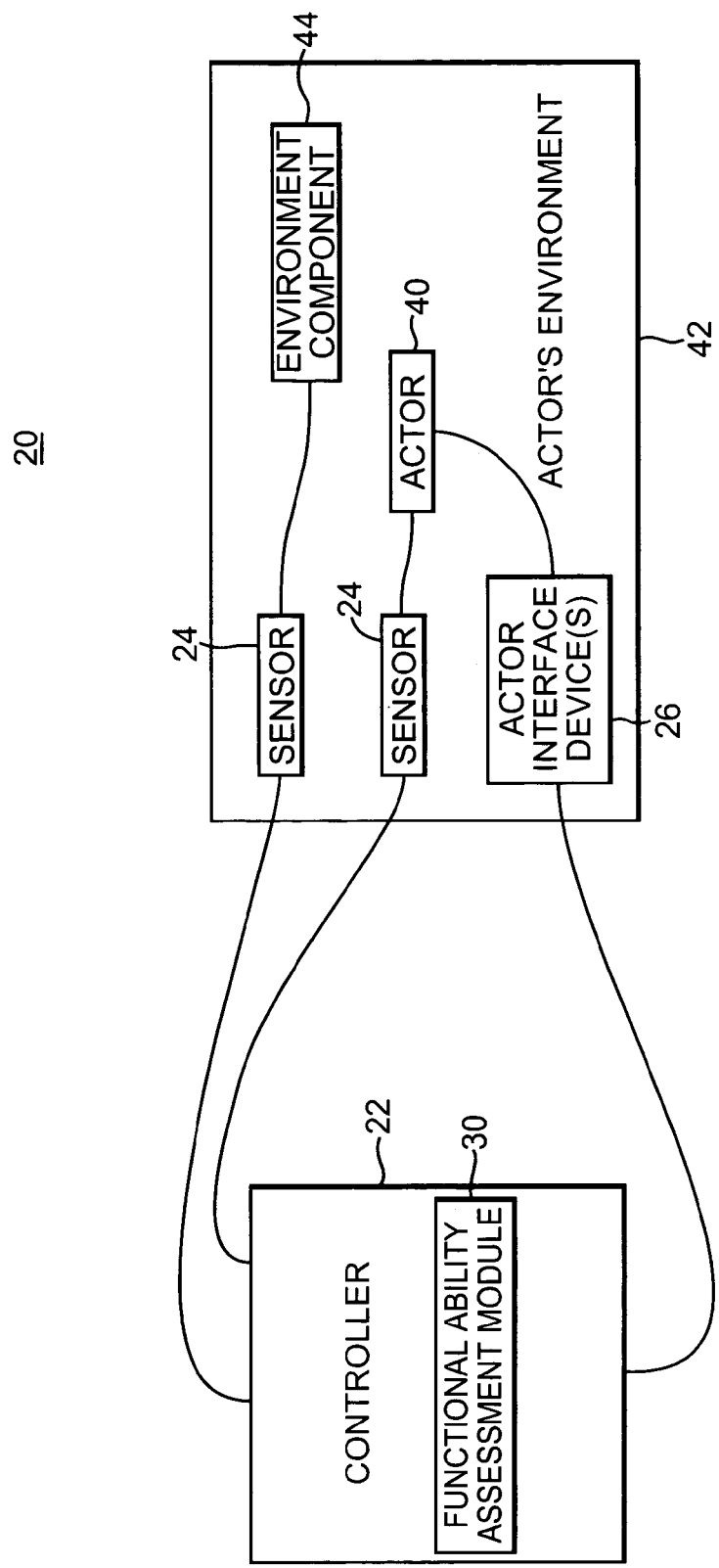
FIG. 1 is a block diagram illustrating a system in accordance with the present invention.

One preferred embodiment of a functional ability assessment system 20 in accordance with the present invention is shown in block form in FIG. 1. In most general terms, the system 20 includes a controller 22, a plurality of sensors 24, and one or more actor interface devices 26 (with the sensor(s) 24 and actor interface device(s) 26 collectively referred to as "data sources"). The controller 22 includes a functional ability assessment module 30, described in greater detail below. The sensors 24 actively, passively, or interactively monitor activities of an actor or user 40 and/or segments of the actor's environment 42, such as one or more specified environmental components 44. Information or data from the sensors 24 is signaled to the controller 22. Similarly, the actor interface device 26 directly interfaces with the actor 40, recording information that the controller 22 and/or the assessment module 30 have requested from the actor 40. The information so-generated is signaled to the controller 22. The functional ability assessment module 30 processes the received information, establishing, maintaining and updating a functional ability database. The recorded information is assessed by the controller 22; and an assessment of the actor's 40 current functional state and/or medical condition (collectively referred to as "functional health") is provided. As part of this evaluation of the actor's current functional health, specific information relating to changes over time can be provided. Additionally or alternatively, the system 20 can provide immediate alerts to a caregiver (not shown) in the event that a significant change in functional ability and/or medical condition is noted. Furthermore, the system 20 can be adapted to specifically watch for a priori symptoms of certain medical problems. For example, the system 20 can monitor for the possible on-set or recent occurrence of stroke via functional information relating to gait, voice, confusion, etc.

The following description of the present invention is with respect to but one acceptable domain of an actor or patient in an in-home or care (e.g., eldercare) daily living environment. Alternatively, the system and method of the present invention are applicable to other domains, such as a workplace, that may be hazardous (e.g., coal mine, space station) or less rigorous, in which one or more actors or workers operate. Thus, any environment in which an actor spends a significant amount of time (e.g., two or more hours) on a regular basis can be considered a "daily living environment", or simply "an environment", of the actor 40 in which the present invention is useful.

The key component associated with the system 20 resides in the modules associated with the controller 22. As such, the sensors 24 and the actor interface device 26 can assume a wide variety of forms. Preferably, the sensors 24 are networked by the controller 22. The sensors 24 can be non-intrusive or intrusive, active or passive, wired or wireless, physiological or physical. In short, the sensors 24 can include any type of sensor that provides information relating to activities of the actor 40 or other information relating to the actor's environment 42, including the environmental component 44. For example, the sensors 24 can include a medication caddy, light level sensors, "smart" refrigerators, water flow sensors, motion detectors, pressure pads, door latch sensors, panic buttons, toilet-flush sensors, microphones, cameras, fall-sensors, door sensors, heart rate monitor sensors, blood pressure monitor sensors, glucose monitor sensors, moisture sensors, telephone sensors, thermal sensors, optical sensors, seismic sensors, etc. In addition, one or more of the sensors 24 can be a sensor or actuator associated with a device or appliance used by the actor 40, such as a stove, oven, television, telephone, security pad, medication dispenser, thermostat, computer interface, etc., with the sensor or actuator providing data indicating that the device or appliance is being operated by the actor 40 (or someone else).

Similarly, the actor interface device 26 can also assume a wide variety of forms. Examples of applicable interface devices 26 include computers, displays, keyboards, web pads, telephones, pagers, speaker systems, etc. In general terms, the actor interface device 26 is configured to interact with the actor 40, requesting specific information and recording responses. For example, the actor interface device 26 can be a "standard" personal computer that presents questions to the actor 40 via a display screen and receives answers via a keyboard entry device. Alternatively, the actor interface device 26 can be akin to a television video game whereby the actor 40 is prompted to participate in a designated game as described below, with the actor's success and response time being recorded. Even further, the interface device 26 can be a home audio system operated to perform a hearing test, a graphical interface adapted to perform a vision test, other medical devices with the capability to output their data and readings electronically (e.g., blood pressure and glucose meters), etc.

Figure 2:
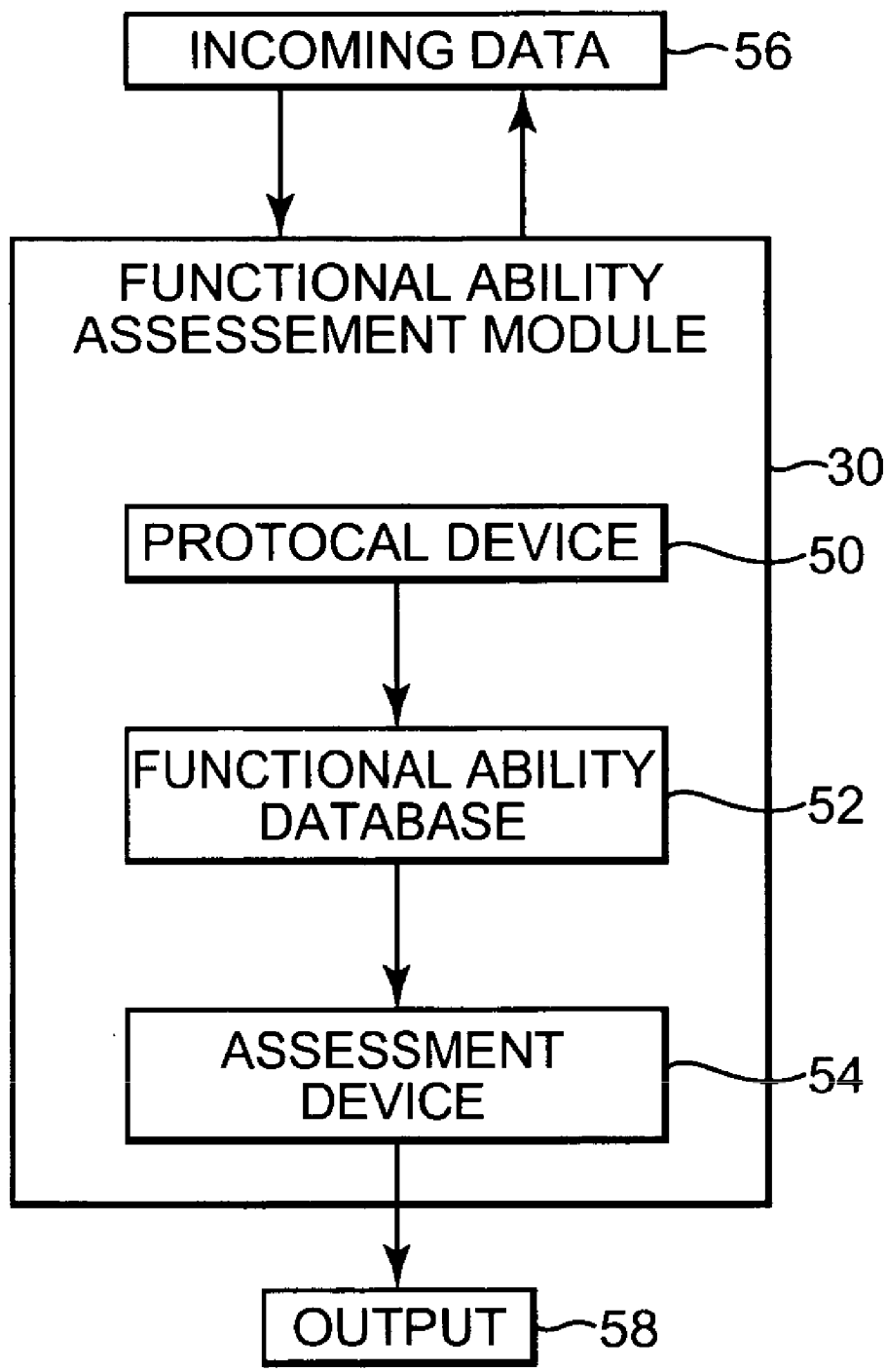
FIG. 2 is a block diagram of a functional ability assessment module in accordance with the present invention.

The controller 22 is preferably a microprocessor-based device capable of storing and operating preferred modules, including the functional ability assessment module 30. The components of the present invention can be implemented in hardware via a microprocessor, programmable logic, or state machine, in firmware, or in software with a given device. Depending upon the complexity of the particular installation, the controller 22 can include and operate a number of additional modules, the relationship of which relative to the functional ability assessment module 30 is described in great detail below. In general terms, however, and with additional reference to FIG. 2, the functional ability assessment module 30 includes in one embodiment a functional ability protocol device 50, a functional ability database 52, and an assessment device 54. The protocol device 50 receives information/data (shown generally in FIG. 2 at 56) from the sensors 24 and/or interface device 26. In this regard, the protocol device 50 can dictate the type(s) of information received and/or the timing at which data is taken; can process all monitoring information generated by the system 20, parsing out information of specific interest; or both. Regardless, information provided through the protocol device 50 is stored in the functional ability database 52. Periodically and/or when requested by a caregiver or other system (not shown), the assessment device 54 reviews and evaluates desired information stored in the database 52, preferably generating an assessment of the actor 40 in terms of medical condition, broad functional ability (i.e., assessment of multiple functional ability categories), or a more limited functional ability assessment (e.g., assessment of a specific actor function such as toileting, sleep, work performance, etc.). The so-generated assessment and/or raw data is provided to a caregiver or other third person or system (referenced generally as "output" at 58). Where desired, the output 58 may come directly from the functional ability database 52.

The manner in which information 56 is provided to the functional ability assessment module 30, as well as assessment techniques performed thereby, is discussed in greater detail below. In general terms, however, the functional ability assessment module 30 is adapted to gather and evaluate data relating to a wide variety of functions. Individual functions can be analyzed individually, or multiple functions can be evaluated together as part of a functional metric or medical condition evaluation. More particularly, the functional ability assessment module 30 preferably organizes gathered data in the database 52 according to baseline functions of interest. Exemplary baseline functions include activities of daily living (ADLs), instrumental activities of daily living (IADLs), medical conditions (vision, hearing, confusion, gait, heart rate, blood pressure, respiration, pain, strength/weakness, blood sugar, etc.), etc. Within each baseline function designation within the database 52, information from one or more sources of data can be stored, depending upon the types of sensor(s) 24 and/or actor interface device(s) 26 provided with the system 20. The actor's overall functional ability or medical condition can then be evaluated based upon an individual baseline function, or upon a combined evaluation of information from two or more baseline functions.

Depending upon the particular baseline function in question, data can be gathered passively by storing signaled information from appropriate ones of the sensor(s) 24 and/or actor interface device(s) 26 within the actor's environment 42. For example, the ADL baseline function of "bathing" can include data obtained from a water sensor in the actor's bathtub and an air quality sensor in the actor's environment 42. Additionally, gathered data can include recorded visual images of the actor 40. For example, information useful in the content of a "mobility" baseline function can include periodic video segments of the actor 40, evidencing the actor's mobility (e.g., walking, transferring, etc.). In this regard, the functional ability assessment module 30 can be adapted to dictate operation of one or more video cameras in the actor's environment 42 so as to provide a desired video segment that is electronically stored in an assigned location of the database 52. In an even more preferred embodiment, the video segment is automatically analyzed/interpreted by an appropriate program, such as video understanding techniques, with the results of this analysis/interpretation being "attached" to the video segment in the database 52. Similarly, other sensor(s) 24 and/or actor interface device(s) 26 may be of a type that generate information relevant to a functional or medical ability evaluation, but only over the course of a relatively short time period (e.g., only 10 seconds of video feed may be necessary to evaluate mobility; an actor's/employee's heart rate while performing a particular job task can be indicative of stress; etc.). The functional ability assessment module 30 can be adapted to retrieve, or prompt signaling of, information from the so-designated data source(s) from or during only the determined time period instead of a continuous long-term string of information. Finally, gathered data can include responses to questions presented to the actor 40 via the interface device 26. For example, a baseline function category of "pain" can include the actor's responses to specific, pre-determined questions relating to pain. Where appropriate, the functional ability assessment module 30 is preferably adapted to present these questions to the actor 40 at appropriate times (and/or a separate module is provided that regulates presentation of questions to the actor 40, in terms of timing, wording, and/or presentation mode). Further, not only can questioning be done to ascertain specific functional abilities (e.g., how are you feeling today?), but also creative questioning can be presented that assist in gauging the actor's functional health.

With the above baseline functions and data gathering techniques in mind, Table 1 below provides a listing of several baseline functions that can be addressed by the functional ability assessment module 30, along with exemplary data sources and related information.

TABLE 1

| Baseline Function | Sample Data Gathering Source/Technique | Related Information |
| --- | --- | --- |
| Transportation | Questions, GPS in car, garage door sensor, acoustic sensor in garage, air quality sensor in garage | |
| Finances | Questions, monitoring online shopping | Bank overdrafts |
| Food preparation | Kitchen motion, utensil drawer, and refrigerator (door) sensor; stove use, water use, video | |
| Laundry | Water sensor, appliance sensor, questions, video | |
| Shopping | Questions, monitoring online shopping | |
| Housekeeping | Sensed activity levels, questions, air quality sensors, video | |
| Telephone Use | Phone off-hook monitor, audio analysis | |
| Dressing | Questions, sensors on dresser, closet, clothes | |
| Bathing | Water in bath sensor, air quality sensor, video | Time in bathroom |
| Grooming | Questions, video | |
| Medications | Medication caddy with sensor, video | Refill records |
| Feeding Self | Kitchen, utensil drawer, refrigerator sensors, questions, dining room video | Toileting |
| Mobility-Ambulation/Stairs/Transfers | Motion sensors, pressure pads, door sensors, video | Control of camera to provide a view that would enable assessment of walking, transferring, |

TABLE 1-continued

| Baseline Function | Sample Data Gathering Source/Technique | Related Information |
|---|---|---|
| | | shaking/reflexes, condition of skin/limbs/arms/legs, etc. |
| Sleep/Rest Patterns | Motion sensors, pressure pads, lights, video | |
| Bladder/Urination Status | Questions, moisture sensors, toilet sensors, motion sensors | |
| Bowel Status | Questions, toilet sensors | |
| Communications/Speech | Questions, speech understanding, voice changes | |
| Vision | Eye test via graphical user interface (if available), questions, machine learning over efficacy of presentation medium | |
| Hearing | Hearing test via home audio interface, questions, machine learning over efficacy of presentation medium | |
| Oral Care | Toothbrush caddy with sensor, questions | Dental records |
| Diet History | Automated scale for weight, questions, toilet chemical analysis, refrigerator inventor, output from appropriate medical devices | |
| Safety | Questions, fall events, intrusion, fraud | |

It should be understood that the baseline functions and data sources referenced in Table 1 are in no way limiting. The functional ability assessment module 30 can track information relating to a number of other functions of interest, and utilize data sources not specifically listed. One particular, additional source of information is monitoring the actor's 40 performance while playing an electronically presented game. Certain diagnostic games provide an indication of mental and/or physical capabilities, such as memory, cognitive mental thinking, hand-eye coordination, etc. Other example baseline functions useful with the present invention can relate to job performance where the actor is an employee in a work place environment.

Figure 3A:
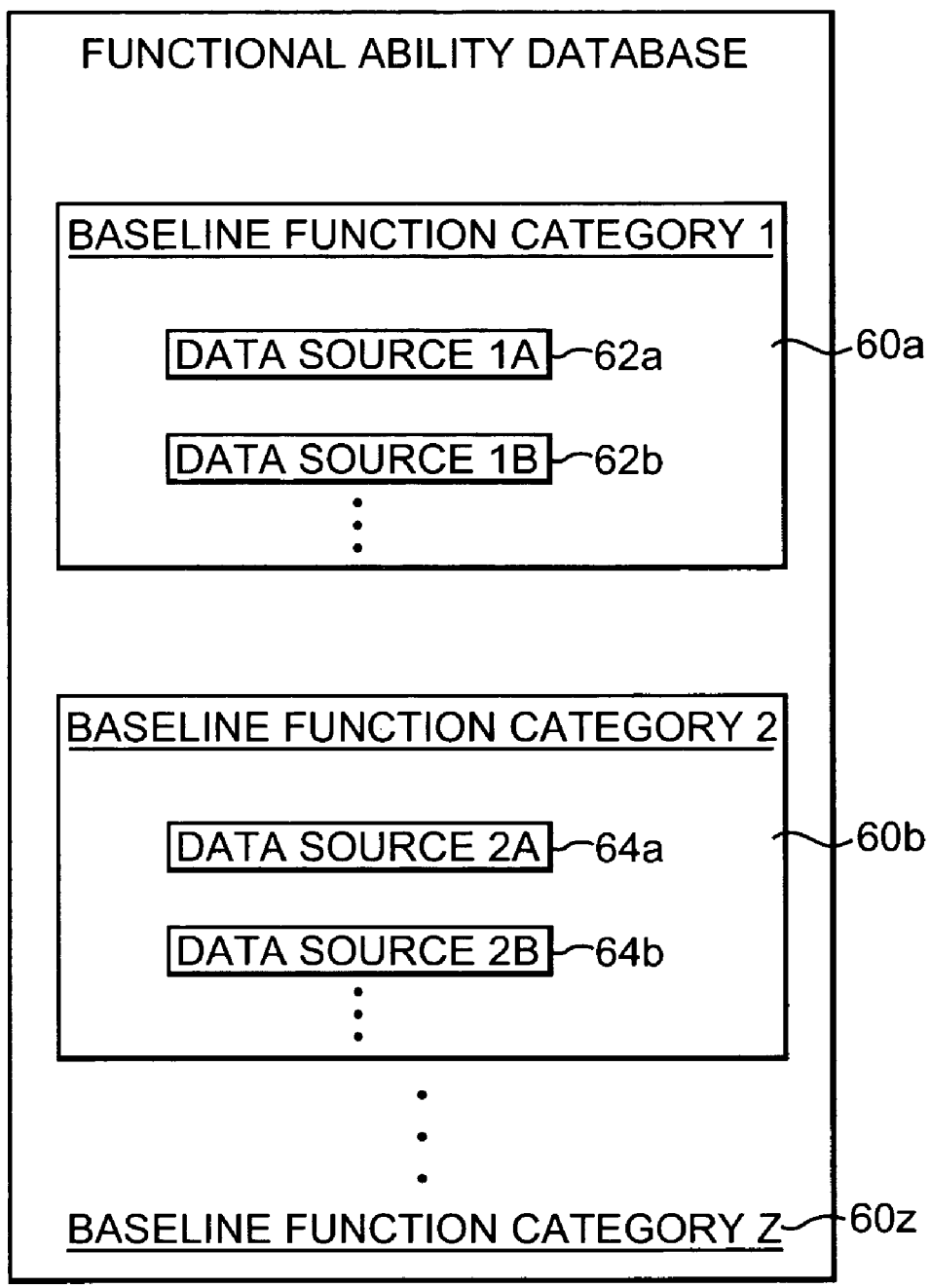
FIG. 3A is a block diagram of a functional ability database in accordance with the present invention.

Regardless of the information source, the functional ability assessment module 30 stores accumulated information in the functional ability database 52. In one preferred embodiment, and with further reference to FIG. 3A, the database 52 organizes accumulated data within pre-assigned baseline function categories (referenced generally at 60a, 60b, 60z). Each baseline function category corresponds with a function of interest; for example, the Baseline Function Category 1 can be "finances" and the Baseline Function Category 2 can be "housekeeping". The database 52 can categorize any number of baseline functions. Within each baseline function category, information from a designated data source(s) is individually stored. For example, where the Baseline Function Category 1 is "finances", data gathered from questions posed to the actor 40 are stored in a source file (or interface source file) as "Data Source 1A" (referenced at 62a), whereas on-line shopping monitoring is stored in a source file as "Data Source 1B" (referenced at 62b). Similarly, where the Baseline Category 2 (60b) is "housekeeping", "Data Source 2A" (referenced at 64a) can be designated as sensed activity levels, whereas "Data Source 2B" (referenced at 64b) includes answers to relevant questions posed to the actor 40. Once again, each Baseline Function Category can include saved information from one or more sources of information. Further, information from a single senor or interface device can be stored in separate source files under two or more different Baseline Function Categories. Regardless, the assessment device 54 (FIG. 2) can readily retrieve information of interest for performing a desired evaluation by referencing the Baseline Function Category or Categories of interest, as described below.

Figure 3B:
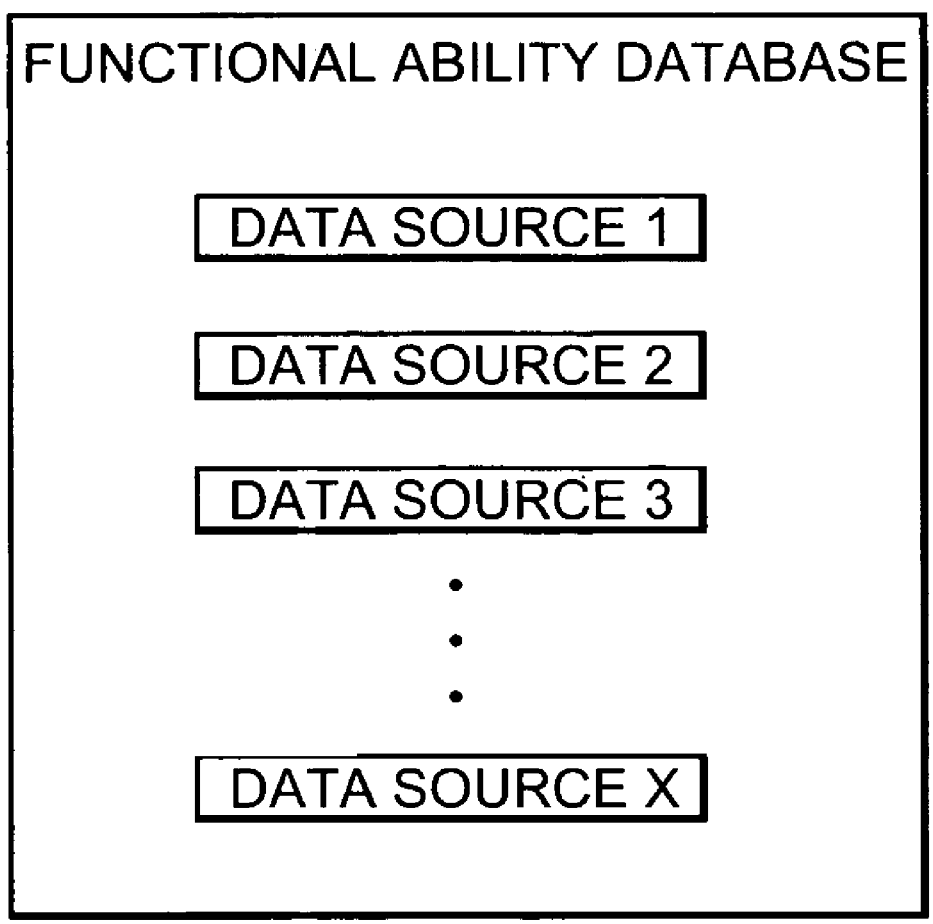
FIG. 3B is a block diagram of an alternative functional ability database.

Alternatively, as shown in FIG. 3B, the functional ability database 52 can store information from multiple data sources in separately designated source files, but without reference to a particular baseline function category. With this approach, the assessment device 54 is adapted to retrieve information from designated data source files within the database 52 in accordance with the particular evaluation being performed. For example, where an evaluation of "mobility" is desired, the assessment device 54 is adapted to retrieve stored information from designated data source(s) corresponding with motion sensors, pressure pads, door sensors, and selected video frames (it being understood that depending upon the type and number of sensors available, some or all of these data sources may not be available and/or information from other data sources employed).

Even further, the functional ability assessment module 30 can be configured to operate without the functional ability database 52. In more generate terms, the functional ability database 52 serves to conveniently accumulate information potentially of interest to one or more functional or medical ability evaluations. However, with certain system 20 configurations, information from each of the data sources 24, 26 is saved over time regardless of whether the functional ability assessment module 30 is present. Under these circumstances, the functional ability assessment module 30, upon determining that a functional or medical ability evaluation is desired, determines which of the data source(s) 24, 26 generate information relating to the evaluation in question (e.g., the functional ability assessment module 30 can be programmed to include designations of which of the data source(s) 24, 26 relate to a particular evaluation; can be programmed to include a general listing of desirable information sources relating to a particular evaluation and then review the system 20 configuration to identify one or more of the data source(s) 24, 26 that might otherwise "match" the "desired" information source list; etc.). The functional ability assessment module 30 then retrieves information from the data base(s) or data source(s) at which the desired information has been stored and/or is being generated. This retrieved information then forms the basis for subsequent functional or medical ability assessment.

Figure 4:
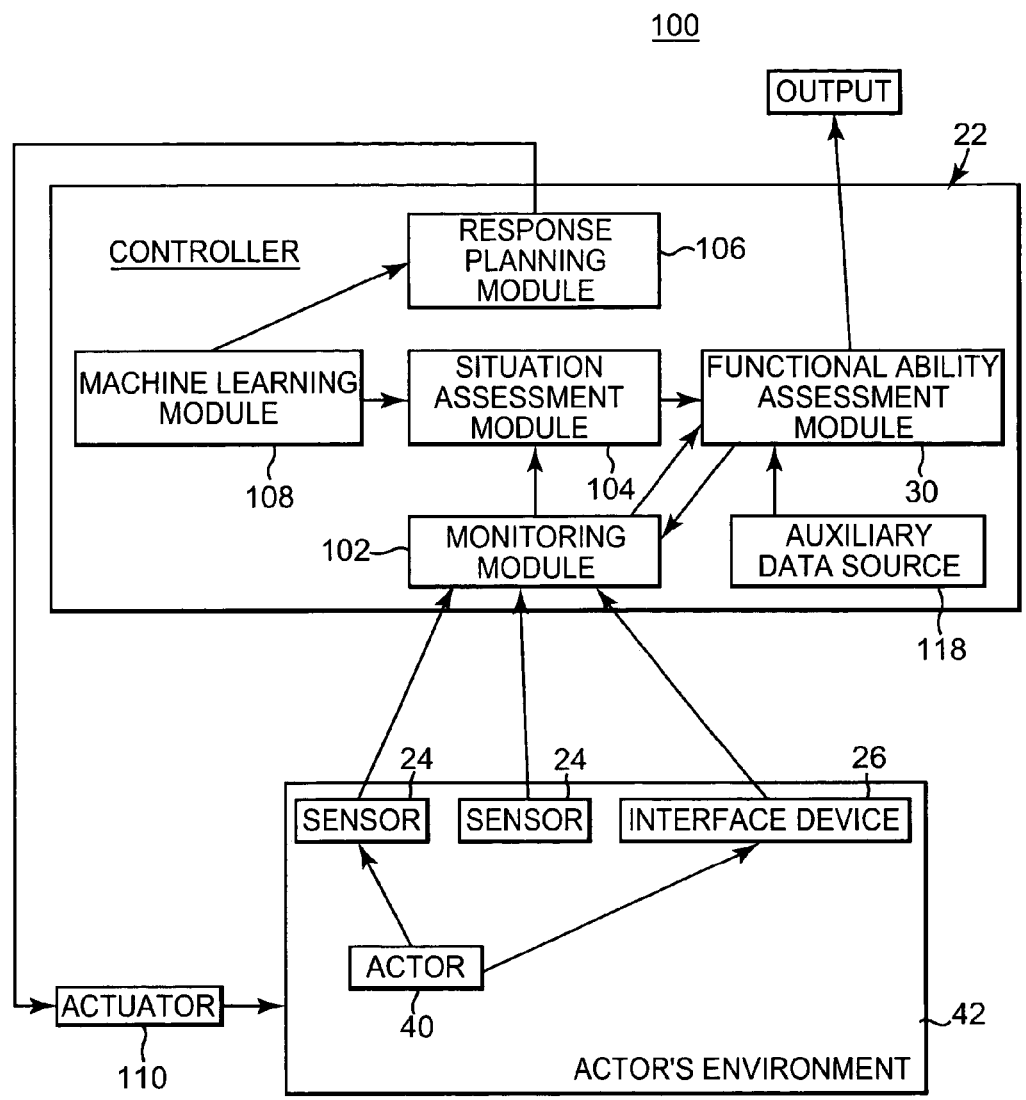
FIG. 4 is a block diagram of an in-home monitoring and response system including a functional ability assessment feature in accordance with the present invention.

Returning to FIG. 1, the manner in which the functional ability assessment module 30 receives information from the various sensors 24 and/or the actor interface devices 26, or directs the sensors 24 and/or the actor interface devices 26 to retrieve data or perform a specific operation (e.g., operating a camera to record video images of the actor 40 walking) is a function of an overall system 20 configuration relative to the actor 40 and the actor's environment 42. In one preferred embodiment, the functional ability assessment system 20 is provided as part of an in-home, automated monitoring and response system 100, shown in block form in FIG. 4. Configuration and operation of the monitoring and response system 100 is provided in greater detail in U.S. application Ser. No. 10/341,355, filed Jan. 10, 2003 and entitled, "System and Method for Automated Monitoring, Recognizing, Supporting, and Responding to the Behavior of an Actor", the teachings of which are incorporated herein by reference. In general terms, the system 100 includes the controller 22 that provides the functional ability assessment module 30 along with other modules such as a monitoring module 102, a situation assessment module 104, a response planning module 106, and an optional machine learning module 108. The provided sensors 24 and the actor interface(s) 26 actively, passively, or interactively monitor activities of the actor 40, as well as segments of the actor's environment 42. Information or data from the sensors 24 is signaled to the controller 22 for interpretation by the monitoring module 102. The situation assessment module 104 processes information from the monitoring module 102 to determine what the actor 40 is doing (and/or intending to do), along with what is happening in the actor's environment 42. One example of an acceptable assessment module is described in U.S. patent application Ser. No. 10/286,398, filed Nov. 1, 2002, the teachings of which are incorporated herein by reference. The response planning module 106, in turn, generates appropriate responses that are carried out via actuators 110. In this regard, the preferred machine learning module 106 "optimizes" operation of the situation assessment module 104 and the response planning module 106, as well as other modules relating to operation of the system 100, based upon automatically generated learned models of behavior formulated from information provided by the sensors 24 and/or the actor interface devices 26. One example of an acceptable machine learning module is described in U.S. patent application Ser. No. 10/339,941, filed Jan. 10, 2003, the teachings of which are incorporated herein by reference.

As part of the above operations, the functional ability assessment module 30 receives actor function ability-related information directly from the monitoring module 102 or indirectly via the situation assessment module 104. In this regard, the functional ability assessment module 30 can be provided as part of the situation assessment module 104. In either case, and with additional reference to FIG. 2, the functional ability protocol device 50 dictates how information presented to the functional ability assessment module 30 is processed. For example, where all monitoring information processed by the situation assessment module 104 is presented to the functional ability assessment module 30, the protocol device 50 can be adapted to review and process this information (e.g., store or not store in the database 52) based upon predefined baseline function categories and/or designated data sources. To this end, the protocol device 50 can be adapted to recognize information being processed by the situation assessment device 104 as relating to one or more of the baseline function categories provided within the database 52 and/or as being generated by a data source of interest. Thus, where the incoming data is provided by a kitchen motion sensor and the database 52 includes a corresponding file location for this information, the kitchen motion sensor information is stored in the database 52. Conversely, where the information being processed relates to operation of a garage door and the database 52 does not include a corresponding category designation, the information can be ignored or stored in a supplemental database available to caregivers (e.g., for review if an anomalous event occurs). The protocol device 50 can be directly linked to the monitoring module 102, again recognizing information streams of interest and storing desired data in a designated fashion in the database 52.

In a more preferred environment, the protocol device 50, either alone or in conjunction with the situation assessment device 104, is adapted to dictate the manner in which data is gathered from the various sources of interest. For example, where a Baseline Function Category 60*a* of "laundry" that includes a designated data source 62*a* of "video of actor doing laundry" is provided with the functional ability assessment module 30, the protocol device 50 can be adapted to prompt operation of a video camera within the actor's laundry room for a short period of time whenever motion is sensed in the laundry room. A digital copy of the short-term video feed (and any computer analysis/interpretation of the video segment, where provided) is then stored in the database 52, along with other related data associated with the "laundry" function. Similarly, the protocol device 50, either alone or in combination with the situation assessment module 104, is preferably adapted to initiate presentation of questions related to functions of interest at appropriate times and in appropriate manners via the actor interface device 26. For example, and again with reference to the exemplary "laundry" Baseline Function Category, the protocol device 50 can initiate presentation of laundry related questions to the actor 40 at predetermined times during the week and/or following occurrence of a designated sensed activity (e.g., sensed activation of a washing machine appliance by one of the sensors 24). The question(s) presented to the actor 40 can be retrieved from an auxiliary data source 118 containing queries specific to the activity in question (e.g., the auxiliary data source 118 can contain "questions about laundry"). The questions can be generated as an output from the functional ability assessment module 30, or via the response planning module 106 that otherwise oversees all outputs from the controller 22. Regardless, the machine learning module 108 preferably operates to adapt the questions and/or timing thereof in a manner most appropriate to the actor 40. Once again, information need not necessarily be stored in a separate functional ability database 52. Instead, for example, the functional ability module 30 can, as part of a functional or medical ability assessment, retrieve information from the data source(s) of interest (either directly or from a separate database related to the desired data source using predetermined guidelines such as the Baseline Function Categories described above).

Figure 5:
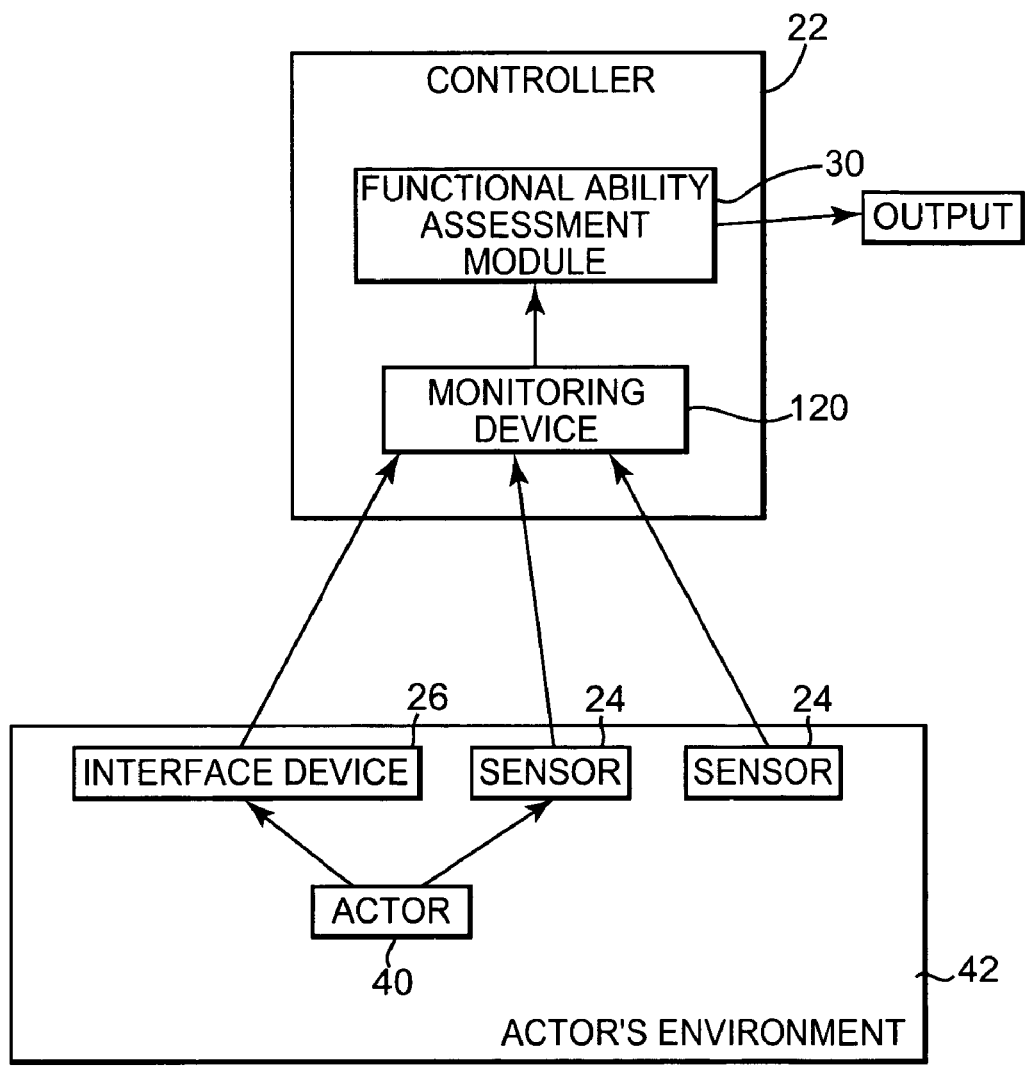
FIG. 5 is a block diagram of a standalone functional ability assessment system.

Although the present invention has described implementation of the functional ability assessment module 30 as part of a complete in-home monitoring and response system, a standalone system can instead be provided. For example, as shown in FIG. 5, the functional ability assessment module 30 can be linked to, or provided as part of, a monitoring device 120 that controls and processes information from the sensor(s) 24 and the actor interface device(s) 26. The output from the functional ability assessment module 30, rather than being used by the complete system, can be provided, for example, directly to a caregiver or employer.

Returning to FIG. 2, a variety of functional ability or medical condition evaluations can be provided by the assessment device 54. The assessment device 54 can perform a trend analysis for individual, designated functions (e.g., can assess the actor's 40 ability to prepare food). Alternatively, two or more tracked functions can be grouped and analyzed. For example, the assessment device 54 can analyze and/or present to a caregiver (not shown) groupings of related information for various metrics, such as a mobility metric. With a mobility metric, the assessment device 54 evaluates and presents a number of different functions including distances traveled by the actor within the environment; gait, speed, and other walking features; various activities engaged in by the actor; video presentations of the actor's movements; etc.

Other possible metrics that can be tracked and reported upon by the functional ability assessment module 30 include a confusion metric that groups and assesses such functions as the actor's performance while playing designated games, monitoring the ease with which the actor is distracted at various points during the day (e.g., length of time to complete a task), and monitoring difficulty of the actor in completing certain different cognitive activities, such as cooking or dressing. Similarly, a dementia metric can be established, whereby information relating to certain functional ability subject matter such as confusion, memory, toileting, and aggression are tracked and stored. A wandering metric can also be provided, with functional ability subject matters such as sundowning (i.e., actor trying to leave the daily living environment when the sun goes down), tracking paths walked by the actor 40, tracking times the actor 40 is walking, etc. are provided. Also, a depression metric can be established that tracks and evaluates functions such as sleep patterns, overall activity, changes in appetite, changes in voice patterns, weight changes, concentration, memory, etc. are established. Further, an alcohol abuse metric can be provided that tracks and evaluates data from sources such as a cabinet sensor, a bottle sensor, breath sensors, wandering, aggression, etc. Furthermore, the assessment module 30 can be adapted to specifically watch for a priori symptoms of certain medical problems. For example, the module 30 can monitor for the possible on-set or recent occurrence of stroke via functional information relating to gait, voice, confusion, etc.

The output 58 from the functional ability assessment module 30 can assume a wide variety of forms, including presentation of requested information via a computer or paper printout. Additionally, the functional ability assessment module 30 can be adapted to signal an alert to a caregiver in the event a significant change in a particular function and/or medical condition is determined.

The system and method of the present invention provides a marked improvement over previous designs. In particular, in-home (or other daily living environment) sensing/actor interface is used to assist in assessing or to assess the functional ability or medical condition of the actor. Because these evaluations occur on-site, they are inherently more accurate then a patient interview that occurs at a remote location. Further, the evaluations are continuous and hence capture minor changes in the actor's capabilities. Thus, a system and method is provided for early detection and possible prevention of acute medical conditions in a manner not heretofore available, with the system essentially serving as an automated diagnosis engine. The system and method of the present invention are also useful in a number of other environment domains; for example, the system and method are capable of assessing employees in a workplace, identifying employees experiencing functional or medical difficulties, and/or employees working at below-expected levels.

Although the present invention has been described with reference to preferred embodiments, workers skilled in the art will recognize that changes can be made in form and detail without departing from the spirit and scope of the present invention.

What is claimed is:

1. A method of assessing functional or medical ability of an actor in an environment comprising:

providing a plurality of data sources in the environment of the actor;

receiving a request to perform an evaluation of a first functional or medical ability;

determining which of the plurality of data sources generate information relating to the first functional or medical ability by comparing each of the plurality of data sources with an electronically stored list of desirable informational sources designated as being relevant to the first functional or medical ability, wherein the determination is made solely by a functional ability assessment module as operated by a processor;

gathering previously-stored data from the data sources determined to generate information relating to the first functional or medical ability;

automatically evaluating the first functional ability of the actor based upon a combined assessment of the gathered data; and forwarding information relating to the evaluation to a third party.

2. The method of claim 1, further comprising:

presenting the evaluation to a third person concerned with the well-being of the actor.

3. The method of claim 1, further comprising:

determining which of the data sources generate information relating to a second functional or medical ability, wherein the determination is made apart from the determination of which of the data sources generate information relating to the first functional or medical ability;

gathering data from the data sources determined to generate information relating to the second functional or medical ability; and automatically evaluating the second functional or medical ability.

4. The method of claim 1, further comprising:

identifying which of the plurality of data sources provides information relating to one or more functional abilities; and recording information from the identified data sources in a functional ability database.

5. The method of claim 4, wherein the recorded information is categorized within the functional ability database.

6. The method of claim 1, further comprising:

establishing a plurality of baseline function categories; and assigning information from at least two of the data sources to at least one of the baseline function categories.

7. The method of claim 6, wherein at least one of the baseline function categories is an activity of daily living (ADL).

8. The method of claim 6, wherein at least one of the baseline function categories is an instrumental activity of daily living (IADL).

9. The method of claim 6, wherein at least one of the baseline function categories is a medical condition.

10. The method of claim 6, wherein at least one of the baseline function categories relates to job performance.

11. The method of claim 6, wherein information from a first one of the data sources is assigned to a first and a second baseline function category.

12. The method of claim 6, wherein evaluating a functional ability of the actor is based upon information from at least two of the baseline function categories.

13. The method of claim 1, further comprising:

establishing a plurality of available ability topics; and correlating at least two of the data sources with one or more of the available ability topics.

14. The method of claim 1, further comprising:
determining that information from a first one of the data sources over a time period is relevant to a functional ability evaluation; and
retrieving information from the first data source for the time period.

15. The method of claim 14, wherein the first data source includes a video camera.

16. The method of claim 1, further comprising:
providing an actor interface device as one of the data sources;
operating the actor interface device to interact with the actor; and
wherein evaluating a functional ability of the actor is based upon information from the actor interface device.

17. The method of claim 16, wherein operating the actor interface device includes:
causing the actor to participate in a game.

18. The method of claim 16, wherein operating the actor interface device includes:
causing the actor to participate in a medical test.

19. The method of claim 16, wherein operating the actor interface device includes:
causing the actor to participate in a plurality of different activities.

20. The method of claim 1, wherein evaluating a functional ability includes performing a trend analysis.

21. The method of claim 1, wherein evaluating a functional ability includes:
analyzing a grouping of information from a plurality of data sources.

22. The method of claim 1, wherein evaluating a functional ability includes:
grouping information from a plurality of data sources; and
presenting the grouping of information.

23. The method of claim 1, wherein evaluating a functional ability includes:
establishing an ability metric combining information from at least two of the data sources; and
assessing information of the ability metric.

24. The method of claim 23, further comprising:
establishing a plurality of ability metrics.

25. The method of claim 1, further comprising:
monitoring for a priori symptoms of a medical problem.

26. The method of claim 25, further comprising:
determining that a medical problem is implicated by at least one of the monitored a priori symptoms; and
generating an alert based upon the determination.

27. The method of claim 1, wherein providing a plurality of data sources includes providing a plurality of sensors.

28. The method of claim 1, wherein the environment is a home.

29. The method of claim 1, wherein the environment is a work place.

30. The method of claim 1, wherein determining which of the plurality of data sources generate information relating to the first functional or medical ability includes:
identifying any of the plurality of data sources that match an entry in the list of desirable informational sources, wherein the identification is performed through a processor.

31. The method of claim 30, wherein generating data includes:
gathering data from only the data sources identified as matching the list of desirable informational sources.

32. The method of claim 1, further comprising:
identifying a first one of the data sources as corresponding with the list of desirable informational sources;
prompting selective operation of the first data source in response to the identification;
collecting data from the first data source during selective operation of the first data source; and
considering the collected data in evaluating the first functional ability.

33. A system for assessing functional or medical ability of an actor in an environment, the system comprising:
a plurality of data sources; and
a controller electronically maintaining a functional ability assessment module and adapted to:
determine which of the data sources generate information relating to a particular functional or medical ability in response to a request for an evaluation of the particular functional or medical ability based upon reference to a stored list of desirable informational sources and without human operator data source selection prompts,
gather data from the determined data sources,
automatically evaluate a functional ability of the actor based upon a combined assessment of the gathered data.

34. The system of claim 33, wherein the controller is further adapted to present the evaluation to a third person.

35. The system of claim 33, wherein the controller includes a plurality of baseline function categories and assigns information from at least two of the data sources to at least one of the baseline function categories.

36. The system of claim 35, wherein information from a first one of the data sources is assigned to at least two baseline function categories.

37. The system of claim 35, wherein the controller is further adapted to generate an evaluation based upon at least two of the baseline function categories.

38. The system of claim 33, wherein the controller is further adapted to:
establish a plurality of available ability topics; and
correlate at least two of the data sources with one or more of the available ability topics.

39. The system of claim 33, wherein the controller further adapted to:
determine that information from a first one of the data sources over a time period is relevant to a functional ability evaluation; and
retrieve information from the first data source for the time period.

40. The system of claim 39, wherein the first data source is a video camera.

41. The system of claim 33, further comprising:
an actor interface device adapted to selectively interact with the actor;
wherein the controller is further adapted to retrieve responses of the actor to operation of the actor interface device for use in evaluating a functional ability.

42. The system of claim 41, wherein the actor interface device is adapted to engage the actor in a game.

43. The system of claim 33, wherein the controller is further adapted to monitor for a priori symptoms of a medical problem.

44. The system of claim 43, wherein the controller is further adapted to:
determine that a medical problem is implicated by at least one of the monitored a priori symptoms.

45. The system of claim 44, wherein the controller is further adapted to:
   generate an alert message in response to a determination that a medical problem has been implicated.

46. The system of claim 33, wherein the plurality of data sources includes at least one sensor.

47. The system of claim 33, wherein the controller maintains a functional ability database, the controller further adapted to:
   store information from selected ones of the data sources in the functional ability database.

48. The system of claim 47, wherein the controller is further adapted to:
   categorize the stored information within the functional ability database.

49. The system of claim 33, wherein the controller is further adapted to:
   generate a model of actor behavior; and
   retrieve information relating to the functional ability according to the model of actor behavior.

50. The system of claim 49, wherein the retrieving information relating to the functional ability according to the model of actor behavior includes the controller adapted to designate a desired timing of information retrieval from the plurality of data sources based upon the model of actor behavior.

* * * * *